(12) United States Patent
Nill et al.

(10) Patent No.: US 9,943,345 B2
(45) Date of Patent: Apr. 17, 2018

(54) MECHANOTRONIC IMPLANT

(71) Applicant: WITTENSTEIN SE, Igersheim (DE)

(72) Inventors: Eduard Nill, Würzburg (DE); Jan Friedmann, Denklingen (DE)

(73) Assignee: WITTENSTEIN SE, Igersheim (DE)

( * ) Notice: Subject to any disclaimer, the term of this patent is extended or adjusted under 35 U.S.C. 154(b) by 0 days.

(21) Appl. No.: 15/183,958

(22) Filed: Jun. 16, 2016

(65) Prior Publication Data

US 2016/0367297 A1 Dec. 22, 2016

(30) Foreign Application Priority Data

Jun. 16, 2015 (DE) .................. 10 2015 109 624

(51) Int. Cl.
| | |
|---|---|
| *A61B 17/56* | (2006.01) |
| *A61B 17/58* | (2006.01) |
| *A61F 2/30* | (2006.01) |
| *A61B 17/72* | (2006.01) |
| *A61B 17/70* | (2006.01) |
| *A61B 17/68* | (2006.01) |
| *A61B 17/00* | (2006.01) |

(52) U.S. Cl.
CPC ...... *A61B 17/7216* (2013.01); *A61B 17/7016* (2013.01); *A61B 2017/00115* (2013.01); *A61B 2017/681* (2013.01)

(58) Field of Classification Search
CPC .............. A61B 17/70; A61B 17/7014–17/7017
See application file for complete search history.

(56) References Cited

U.S. PATENT DOCUMENTS

| 4,931,055 A * | 6/1990 | Bumpus ............. A61B 17/8004 |
| | | 606/254 |
| 5,350,379 A | 9/1994 | Spievack |
| 5,626,579 A * | 5/1997 | Muschler ........... A61B 17/7216 |
| | | 606/60 |
| 5,626,581 A * | 5/1997 | Staehlin ............. A61B 17/7216 |
| | | 606/53 |
| 5,961,553 A | 10/1999 | Coty et al. |
| 7,753,915 B1 * | 7/2010 | Eksler .................. A61B 17/663 |
| | | 606/105 |
| 8,092,499 B1 * | 1/2012 | Roth ................... A61B 17/7004 |
| | | 606/254 |

(Continued)

FOREIGN PATENT DOCUMENTS

| DE | 69407760 T2 | 9/1998 |
| DE | 19717357 A1 | 2/1999 |

(Continued)

*Primary Examiner* — Eduardo C Robert
*Assistant Examiner* — Michelle C Eckman
(74) *Attorney, Agent, or Firm* — Meunier Carlin & Curfman LLC

(57) ABSTRACT

Mechanotronic implant for use in the human body, with a first element, a second element, a drive unit, which is connected in fixed manner to the first element, wherein the drive unit contains an output unit which is connected to the second element in order to move the second element relative to the first element, an implantable energy receiver connected to the drive unit for wireless powering of the drive unit with energy, and a switch in order to switch the drive unit from a first operating direction to a second operating direction.

9 Claims, 2 Drawing Sheets

(56) References Cited

U.S. PATENT DOCUMENTS

| | | | | |
|---|---|---|---|---|
| 8,585,740 | B1* | 11/2013 | Ross | A61B 17/66 606/258 |
| 8,876,870 | B2* | 11/2014 | Qureshi | A61B 17/7061 606/279 |
| 9,113,967 | B2* | 8/2015 | Soubeiran | A61B 17/7014 |
| 9,138,266 | B2 | 9/2015 | Stauch | |
| 9,179,938 | B2* | 11/2015 | Pool | A61B 17/7016 |
| 2003/0080870 | A1* | 5/2003 | Marmaropoulos | H04B 1/385 340/573.1 |
| 2004/0147928 | A1* | 7/2004 | Landry | A61B 17/1671 606/86 A |
| 2006/0009767 | A1* | 1/2006 | Kiester | A61B 17/7004 606/258 |
| 2006/0079897 | A1* | 4/2006 | Harrison | A61B 17/66 63/900 |
| 2006/0195087 | A1* | 8/2006 | Sacher | A61B 17/7014 606/258 |
| 2006/0250203 | A1* | 11/2006 | Marmaropoulos | H01H 15/16 335/205 |
| 2007/0049943 | A1* | 3/2007 | Moskowitz | A61B 17/0642 606/279 |
| 2009/0112207 | A1* | 4/2009 | Walker | A61B 17/7016 606/57 |
| 2010/0114103 | A1* | 5/2010 | Harrison | A61B 17/7016 606/90 |
| 2010/0121323 | A1* | 5/2010 | Pool | A61B 17/7004 606/54 |
| 2011/0196435 | A1 | 8/2011 | Forsell | |
| 2012/0035656 | A1* | 2/2012 | Pool | A61B 17/7004 606/246 |
| 2012/0130428 | A1* | 5/2012 | Hunziker | A61B 17/7016 606/258 |
| 2012/0245636 | A1* | 9/2012 | Dall | A61B 17/7016 606/246 |
| 2013/0338713 | A1* | 12/2013 | Kawakami | A61B 17/7014 606/258 |
| 2014/0128868 | A1* | 5/2014 | Harrison | A61B 17/7016 606/60 |
| 2014/0236234 | A1* | 8/2014 | Kroll | A61B 17/7014 606/264 |
| 2014/0296918 | A1* | 10/2014 | Fening | A61B 17/7016 606/258 |
| 2014/0358150 | A1* | 12/2014 | Kaufman | A61B 17/025 606/90 |
| 2016/0199101 | A1* | 7/2016 | Sharifi-Mehr | A61B 17/7017 606/258 |
| 2017/0095273 | A1* | 4/2017 | Lynch | A61B 17/7014 |

FOREIGN PATENT DOCUMENTS

| | | |
|---|---|---|
| DE | 69600837 T2 | 5/1999 |
| DE | 102008036689 A1 | 2/2010 |
| EP | 2422731 A1 | 2/2012 |
| EP | 2570092 A2 | 3/2013 |
| WO | 2010/050890 A1 | 5/2010 |

* cited by examiner

MECHANOTRONIC IMPLANT

CROSS-REFERENCE TO RELATED APPLICATIONS

This application claims the benefit of German Patent Application No. 102015109624.2, filed on Jun. 16, 2015, the disclosure of which is expressly incorporated herein by reference in its entirety.

FIELD OF THE INVENTION

The invention concerns a mechanotronic implant, especially an intramedullary pin.

PRIOR ART

Mechanotronic implants are known in the prior art. In particular, implants are known which have a drive unit, by which a first element of the implant can be moved relative to a second element, for example, for the distraction of a long tubular bone.

From EP 2 570 092 a system is known in which an intramedullary pin with a drive unit is inserted into the bone in order to lengthen a long tubular bone or restore lost bone material, for example, after the treatment of a tumor. Such systems require a control system which gradually readjusts the length of the intramedullary pin, for example, each day it lengthens the intramedullary pin by 1 mm by activating the drive unit.

Typical implants in normal operation only allow one direction of movement. Depending on the application, this may be limiting. More complex systems which have for example a control software in the implant can provide a remedy here, but they are more difficult to monitor and on occasion they are not sufficiently reliable or require complicated test methods for their marketing authorization.

DISCLOSURE OF THE INVENTION

The problem which the invention proposes to solve is the indication of an implant or an intramedullary pin which is improved as compared to the prior art, having in particular an improved applicability or greater comfort for patients with the most reliable possible functioning.

The problem is solved with an implant according to main claim 1.

One aspect of the invention concerns a mechanotronic implant for use in the human body with a first element, a second element, a drive unit which is connected in fixed manner to the first element, wherein the drive unit contains an output unit which is connected to the second element in order to move the second element relative to the first element, an implantable energy receiver connected to the drive unit for wireless powering of the drive unit with energy, and with a switch in order to switch the drive unit from a first operating direction to a second operating direction.

Typically the second element is moved relative to the first element along a direction of movement, for example, in linear manner. In other sample embodiments, the second element is moved by rotation or a combination of linear-rotary movement relative to the first element. A linear movement can occur, for example, along a longitudinal axis of an orthopedic implant capable of distraction, such as an intramedullary pin.

The energy receiver is typically designed for wireless powering of the drive unit with energy from outside the body. Energy can be transmitted wirelessly in certain embodiments, such as by induction or by capacitive or mechanical coupling.

Typical embodiments comprise an implantable feedback device for indicating whether the drive unit is being operated in the first direction of operation or in the second direction of operation. Typically the indication is wireless. This provides the effect that a wireless feedback as to the direction of operation is possible, in addition to a wireless energy transmission. Typically the indication is to the outside of the body. Typical wireless indicators or feedback devices for the wireless indication include devices for the transmission of light, electromagnetic waves, or mechanical vibrations.

Typical embodiments comprise a feedback device which is designed for a transmission free of radio waves. This offers the effect that a return channel of the feedback device is not dependent on radio waves, just like a control channel for the controlling of the mechanotronic implant. This can improve the operating safety.

Typically the feedback device in certain embodiments is chosen from: an acoustic signal transmitter, an optical signal transmitter or a vibration signal transmitter. An acoustic signal transmitter offers the effect that it can be easily constructed; an optical signal transmitter is perceivable even during loud surrounding noises; and a vibration signal transmitter works independently of sound or light and can be felt in certain embodiments even by the patients themselves through corresponding subcutaneous nerves.

In typical embodiments, the feedback device together with the energy receiver is arranged in an implantable housing. Typically, the feedback device together with the energy receiver and together with the switch is arranged in an implantable housing. This offers a compact design.

In certain embodiments a signal put out by a signal transmitter of the feedback device is modulated, for example, an acoustic signal or optical signal is modulated. Such modulation can involve, for example, a particular sequence of temporary signal interruptions or different tone levels or different light intensities. In this way, additional information such as information on a speed of movement or an expenditure of force or energy required for a movement can be communicated.

Typically the feedback device is designed to communicate information on a speed of movement brought about by the drive unit of the second element relative to the first element. A signal modulation can be used for this, for example, different tone levels, different light intensities, or pulse-pause methods.

In typical embodiments, the switch is chosen from: a reed contact, a photodiode, a capacitor and an electromechanical pressure switch. When a capacitor is used, the skin can be used as a dielectric. Photodiodes respond to light stimulus from the outside, e.g., extracorporally, whereas electromechanical pressure switches can be activated by mechanical action.

In typical embodiments, the drive unit comprises an electric machine and/or a gearing. Electric drive units offer the effect of being especially compact in design and clean. With gearings, an especially large force can be achieved with a small electric drive unit.

Typical embodiments of mechanotronic implants are configured as an intramedullary pin or a scoliosis treatment appliance. Especially in the case of implants which serve to move bone pieces relative to each other, information about the direction of movement is helpful, since as a rule only very small movements are or can be performed in each step, so as not to overload the bones. With such small movements it is not at first glance apparent what the direction of such a movement is. In such applications, feedback devices for information about the direction of movement are of great benefit.

Typically the energy receiver is connected to the drive unit by a cable at least 10 cm long, in other applications a cable at least 15 cm long or at least 20 cm long. In this way, a subcutaneous implantation of the energy receiver, optionally together with the feedback device and/or the switch in a housing, can be implanted subcutaneously, so that an optical feedback through the skin, for example, is also possible.

BRIEF DESCRIPTION OF THE DRAWINGS

Further benefits and features of preferred embodiments of the invention will be explained below by means of the accompanying drawings, where the figures show.

DESCRIPTION OF TYPICAL SAMPLE EMBODIMENTS

Figure 1:
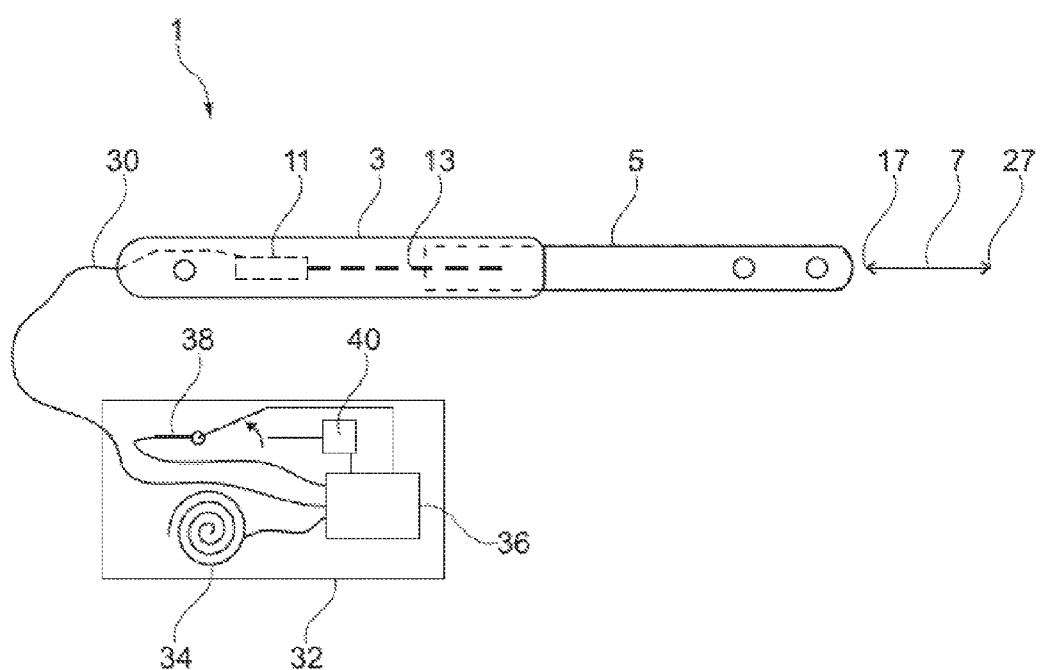
FIG. 1 shows in a schematic view one embodiment of the invention.

FIG. 1 shows a mechanotronic implant 1, representing a typical embodiment.

The mechanotronic implant 1 is configured as an intramedullary pin and comprises a first element 3 and a second element 5. The first element 3 is at least partly hollow and partly receives the second element 5, so that the second element 5 can be displaced in and out of the first element 3 along one direction of movement 7. The mechanotronic implant 1 of FIG. 1 is an adjustable intramedullary pin which can be used for distraction of long tubular bones.

Typical embodiments of the invention involve adjustable intramedullary pins as mechanotronic implants, other embodiments comprise devices for scoliosis treatment or other mechanotronic implants which can perform movements in the body.

The mechanotronic implant 1 of FIG. 1 comprises a drive unit 11, which has a spindle as the output unit 13. The output unit 13 is fixed to the second element 5. The drive unit 11 is fixed to the first element 3 or received in a housing or a hollow cylinder of the first element 3.

By activating the drive unit 11, a movement of the output unit 13 occurs, in order to move the second element 5 along the direction of movement 7, which runs in the longitudinal direction of the mechanotronic implant.

The drive unit 11 is designed to move the second element 5 relative to the first element 3 in a first direction of movement 17 and in a second, opposite direction of movement 27. The directions of movement 17 and 27 run along the axis of movement 7.

Typical embodiments comprise a drive unit which is designed as an electric machine. Other embodiments comprise hydraulic drive units.

The mechanotronic implant 1 furthermore comprises an energy receiver 32 connected by a cable 30 which is 20 cm long to the drive unit. The energy receiver 32 comprises a housing, in which a coil 34 is arranged, which is suited to receiving energy by inductive energy transmission.

The housing of the energy receiver 32 can be implanted in a patient's body, typically subcutaneously. Thanks to inductive energy transmission making use of the coil 34, it is possible to supply energy to the energy receiver 32.

Moreover, the energy receiver 32 has a connection unit 36, at which a switch 38, the coil 34 and a piezo-buzzer 40 make electrical contact with each other.

The switch 38 can be designed in certain embodiments as a reed contact, which can be activated extracorporally by means of a magnet. Under the terms "reed contact" and "switch" also fall combinations of several reed contacts, such as two reed changeover contacts for reversal of polarity. By activating the switch 38, a corresponding switching can be implemented in the connection unit 36, so that the direction of movement is changed along the movement axis 7, for example, from the first direction of movement 17 to the second direction of movement 27 when the switch is closed and from the second direction of movement 27 to the first direction of movement 17 when the switch 38 is opened.

In typical embodiments, the energy receiver 32 has the piezo-buzzer 40 inside its housing, which is activated if the switch 38 is closed and if current is flowing through the switch 38, for example, when electromagnetic energy is applied to the coil 34.

Typically the connection unit is realized purely by hardware, i.e., it has no software. This offers the benefit of high reliability of a simple design and also possibly simplified test methods for an application in the medical field when verifying the technical reliability of the mechanotronic implant.

Further embodiments comprise a central control unit of the connection unit, wherein the central control unit can operate by software. This offers the benefit that reprogramming is possible.

In other embodiments, other switches are provided as the reed contact of the switch 38 or other feedback devices as the piezo-buzzer 40 of the sample embodiment of FIG. 1. Further examples are mentioned in another place in this application. Basically, the representation of FIG. 1 is highly schematic, especially in regard to the switch 38. A more precise representation of an embodiment shall be described hereafter in connection with FIG. 2.

Figure 2:
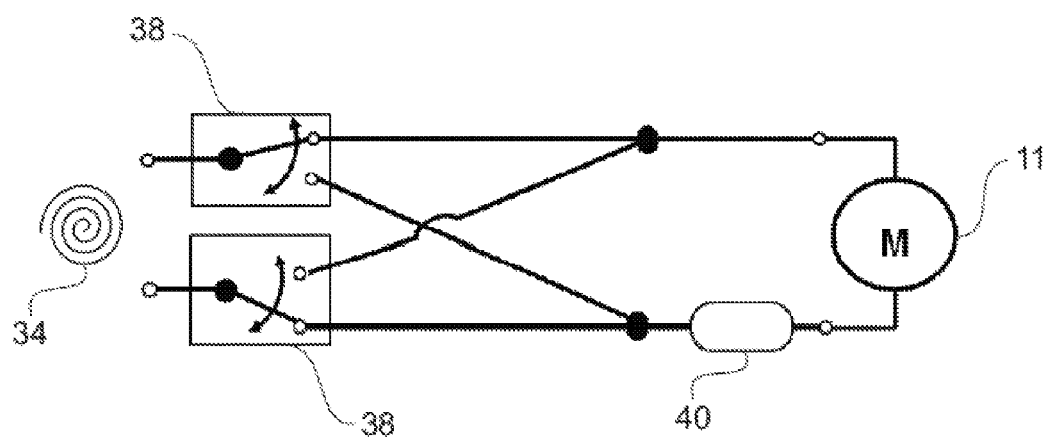
FIG. 2 shows a configuration of a detail of the sample embodiment of FIG. 1 in another schematic view.

FIG. 2 shows one possibility of the switching which can be realized by the connection unit and which is used in typical embodiments. The parts already described in the context of FIG. 1 shall not be explained once more, but instead reference numbers shall be used for identical parts.

The coil 34 is connected to the switch 38, which is designed for example in the form of two reed changeover contacts. This makes possible a reversal of polarity and thus a change in the running direction of the drive unit 11. For this, both reed changeover contacts are operated at the same time. Thus, the activation makes possible a change of direction between the first direction of movement 17 and the second direction of movement 27.

In certain embodiments the switch is provided with a plurality of reed contacts. In other embodiments, an electronic component can be used to achieve a reversal of polarity and thus a change in the running direction of the drive unit. A typical embodiment uses only one reed contact, which actuates an electronic component that is hooked up between coil and drive unit and reverses polarity of the motor when the switch is activated, thereby changing its direction of rotation.

Depending on the activation of the reed changeover contacts of the switch 38, a piezo-buzzer 40 as feedback device hooked up in series with one of the reed changeover contacts is activated or energized. By activating the piezo-buzzer 40 it is possible to perceive corresponding acoustic signals in a subcutaneous implantation even outside the body. Furthermore, it may be possible in certain embodiments for the patient himself to feel the vibration and provide feedback accordingly. Certain embodiments can comprise a piezo-buzzer connected to an electronic component or a piezo-buzzer which is provided with a freewheeling diode so as to generate a signal only for a particular polarity.

The different running direction of the electric machine of the drive unit can be achieved in certain embodiments in that an intermediate voltage circuit with negative polarity is created, and typically a piezo-buzzer or another indicator device is permanently arranged in the negative-polarity intermediate voltage circuit or the positive-polarity intermediate voltage circuit. In the case of a polarity with intermediate switched piezo-buzzer, a signal of the piezo-buzzer can be heard outside the body, especially with a stethoscope.

Thanks to the simple design, there are few if any restrictions on authorization in the field of medical technology.

Typically a reed contact can be switched by a magnet applied outside the body. The term "reed contact" also basically includes reed changeover contacts which can be distinguished in making possible a reversal of polarity. In typical embodiments, the reed contact and/or the piezo-buzzer can be mounted on a shared electronic circuit card, especially together with a coil for an energy reception. This offers a compact design.

In certain embodiments the piezo-buzzer is activated in both directions of movement, for example, with different timing and/or different tone level and/or different tone sequence.

One possibility is a timing of the drive unit, for example, an operation for 2 seconds with interruptions of 1 second in one direction and an operation for 1 second with interruptions of 2 seconds in the other direction. In this way, different directions of movement can be detected from the outside, especially with a stethoscope.

In the preceding description, typical sample embodiments have been explained with the help of figures, but the invention is not confined to these sample embodiments; instead, the scope of the invention is determined by the claims.

The invention claimed is:

1. A mechanotronic implant for use in the human body, comprising:
    a first element;
    a second element;
    a drive unit, which is connected in a fixed manner to the first element, wherein the drive unit contains an output unit which is connected to the second element in order to move the second element relative to the first element;
    an implantable energy receiver connected to the drive unit for wireless powering of the drive unit with energy;
    a switch in order to switch the drive unit from a first operating direction to a second operating direction; and
    an implantable feedback device for indicating whether the drive unit is being operated in the first direction of operation or in the second direction of operation, wherein the feedback device is designed for a transmission free of radio waves, and wherein the feedback device is an acoustic signal transmitter.

2. The mechanotronic implant according to claim 1, wherein the feedback device together with the energy receiver is arranged in an implantable housing.

3. The mechanotronic implant according to claim 1, wherein the feedback device is designed to communicate information regarding the speed of movement, as determined by the drive unit between the second element relative to the first element.

4. The mechanotronic implant according to claim 1, wherein the switch is chosen from: a reed contact, a photodiode, a capacitor and an electromechanical pressure switch.

5. The mechanotronic implant according to claim 1, wherein the drive unit comprises an electric machine and/or a gearing.

6. The mechanotronic implant according to claim 1, which is configured as an intramedullary pin or a scoliosis treatment appliance.

7. The mechanotronic implant according to claim 1, wherein the energy receiver is connected to the drive unit by a cable at least 20 cm long.

8. The mechanotronic implant according to claim 1, wherein the feedback device only transmits a signal in case the drive unit is being operated in the first direction of operation and does not transmit a signal in case the drive unit is being operated in the second direction of operation to indicate the direction of operation.

9. A mechanotronic implant for use in the human body, comprising:
    a first element;
    a second element;
    a drive unit, which is connected in a fixed manner to the first element, wherein the drive unit contains an output unit which is connected to the second element in order to move the second element relative to the first element;
    an implantable energy receiver connected to the drive unit for wireless powering of the drive unit with energy,
    a switch in order to switch the drive unit form a first operating direction to a second operating direction, wherein the switch is chosen from: a reed contact, a photodiode, a capacitor, and an eletromechanical pressure switch; and
    an implantable feedback device for indicating whether the drive unit is being operated in the first direction of operation or in the second direction of operation, wherein the feedback device is designed for a transmission free of radio waves.

* * * * *